United States Patent [19]

James

[11] Patent Number: 4,837,434

[45] Date of Patent: Jun. 6, 1989

[54] MASS SPECTROMETRY SYSTEM AND METHOD EMPLOYING MEASUREMENT/SURVEY SCAN STRATEGY

[75] Inventor: Craig A. James, Palo Alto, Calif.

[73] Assignee: Hewlett-Packard Company, Palo Alto, Calif.

[21] Appl. No.: 71,492

[22] Filed: Jul. 9, 1987

[51] Int. Cl.⁴ .............................................. H01J 49/00
[52] U.S. Cl. .................................... 250/281; 250/282; 250/288
[58] Field of Search ........... 250/281, 282, 288, 288 A; 356/308

[56] References Cited

U.S. PATENT DOCUMENTS

| | | | |
|---|---|---|---|
| 3,639,738 | 2/1972 | Laukien | 324/77 CS |
| 4,008,388 | 2/1977 | McLafferty et al. | 250/288 |
| 4,507,555 | 3/1985 | Cheng | 250/281 |

*Primary Examiner*—Carolyn E. Fields
*Assistant Examiner*—John A. Miller

[57] ABSTRACT

A gas chromatography plus mass spectrometry system implements a scan strategy in which each full range scan alternates between a normal measurement mode and a survey mode based on a block/gap map made during the previous scan. Survey mode is used within regions that were determined in the previous scan to lack signal above a predetermined threshold. Spectral data is generated during measurement mode operation. Each scan serves both measurement and mapping functions in a way that avoids mass filter jumps, since each scan is monotonic over the entire scanning range.

8 Claims, 2 Drawing Sheets

MASS SPECTROMETRY SYSTEM AND METHOD EMPLOYING MEASUREMENT/SURVEY SCAN STRATEGY

BACKGROUND OF THE INVENTION

The present invention relates to measurement systems and methods, and, more particularly, to a system and method providing for increased temporal peak-shape resolution in a mass spectrometer.

A primary objective of the present invention is to provide a strategy which optimizes the scan cycle time for a monotonically scanning instrument for a given range and accuracy. While the invention has particular applicability to mass spectrometry in conjunction with gas chromatography, the invention applies to other applications with similar considerations.

Mass spectrometry is a method of analyzing a gaseous sample by ionizing the constituent molecular components and separating these components according to mass-to-charge ratios. Generally, mass spectrometers include mass filters which use electric or magnetic fields to filter out all but a selected mass-to-charge ratio at a collector.

At any given instant, a mass spectrometer detects only molecules with the mass-to-charge ratio determined by the applied field. A complete mass spectrum for a sample is obtained by varying the field so that molecules with different mass-to-charge ratios are detected at different times. The collector output can be plotted against mass-to-charge ratio.

Mass spectrometers can be used in applications such as gas chromatography in which scanning speed is critical. Gas chromatography usually involves the separation of gaseous mobile phase sample components passed over a stationary phase mesh. Different sample components are retained to different degrees, causing them to elute at different times. Upon arrival of at the chromatograph's effluent end, they are introduced into a mass spectrometer.

For even minimal spectral quality of the resulting gas chromatogram, the mass spectrometer must perform two complete scans per chromatographic component peak. Characterizing chromatographic peak shapes requires more than two complete scans per component peak; four to seven scans are usually adequate. Where chromatographic peaks are unresolved, i.e., elute during overlapping intervals, even greater numbers of mass spectral scans are required to permit reliable mathematical deconvolution of the chromatogram.

Higher frequency cycling can be achieved by compromising one or more alternative performance criteria. One can reduce the mass range of the spectrometer; scan a given range with grosser steps while reducing the selectivity of the mass filter at the cost of mass resolution; or spend less time per measurement, with a concomitant loss in signal-to-noise ratio, and, therefore, accuracy.

In practice, improved cycling frequency without comparable tradeoffs in range, mass resolution and accuracy is achievable due to the fact that most mass spectra are primarily empty. For example, a typical sample might be represented by detections at 20-100 masses with a typical spectrometer range of 50-800 daltons. (A "dalton" is one-twelfth the mass of the common carbon isotope $C^{12}$, practically equivalent to one atomic mass unit). Accordingly, the objective of achieving higher cycling frequency can be attacked with strategies for eliminating the waste involved as a spectrometer carefully measures nothing.

In the absence of such a strategy, an illustrative mass spectrometer might scan from 800 daltons to 50 daltons in one-tenth dalton decrements at 800 daltons per second, yielding a 1 Hz cycle time, or 1 second temporal resolution. By way of contrast, a simple dual-mode, survey/measurement, scan strategy precedes each normal measurement scan with a ten times faster survey scan. The low resolution survey scan suffices to exclude empty areas from the succeeding measurement scan. Thus, the measurement scan might only apply to about one third of the mass spectrum. Including the time for the survey scan and the intermediate backscan, such a strategy generally yields a significant improvement over a single-mode scan strategy.

A constraint on dual-mode strategies is that mass filters of mass spectrometers typically require stabilization prior to making a measurement. Abrupt changes in the mass being scanned incur considerable overhead in invalid measurements or stabilization time. The time required for instrument stabilization is minimized when scanning is gradual and monotonic. This is the typical approach used in single-mode measurement. Stabilization time requirements increase with upward scanning and with "hopping" between non-adjacent masses.

The performance of the simple dual-mode strategy described above is adversely affected by the requirement for stabilization. The larger and faster the leap, the greater the stabilization time required. Furthermore, once the survey is obtained, the skipping of blank spaces in the spectrum still consumes time. Thus, in the simple dual-mode strategy, blank areas consume scan time both during the survey scan and during measurement scan.

Other dual-mode strategies include a survey mode which switches to a measurement mode when a peak is detected. This generally involves backing up or jumping the mass filter, requiring additional stabilization time. Thus, while there are many strategies that afford an improvement over a single measurement mode, none of the available strategies is effectively optimized with respect to the stabilization requirements of mass filters. What is needed is a strategy which is well adapted to the stabilization requirements of mass spectrometers so as to optimize the scan cycling frequency.

SUMMARY OF THE INVENTION

In accordance with the present invention, individual monotonic scans of a mass spectrometer, or an analogous instrument, provide for switching between a measurement mode and a survey mode as a function of data collected during the preceding scan. Data collected during the measurement mode is used to construct a mass spectrum. Data collected during both the survey mode and the measurement mode is used to form a signal/blank map of the spectrometer range to distinguish mass regions where the signal strength is above or below a predetermined threshold. The map is used to determine mode usage during the next scan, the survey mode being used within blank regions and the measurement mode being used in the signal regions. A mass spectrometer in accordance with the invention includes means for generating and storing signal/blank maps. In addition, the spectrometer must include means for executing mode switching in accordance with the generated maps.

Preferably, the mass filter of the mass spectrometer provides precise control over the mass and resolution of the measurements. In particular, the mass filter should have a peak width which is variable for a given mass. The survey mode scans faster than the measurement mode. Preferably, the survey mode involves larger steps, a greater peak width and a lower threshold. The larger steps provide the faster scan rate, while the increased peak width ensures that the larger steps do not skip data. The lower threshold compensates in part for the lower specificity of the survey mode and promotes capture of peaks which grow between the present and the next scan.

Although survey mode scanning produces poorly resolved spectra, the results are sufficient to determine where a spectrum is empty. This provides a basis for a subsequent look at interesting areas in detail while skipping empty parts, which usually constitute most of a spectrum.

As indicated above, mass filters do not stabilize quickly after abrupt mass changes. The present strategy causes the mass filter to speed up and slow down many times per scan, but once a scan starts it proceeds monotonically to the finish. A scan is "monotonic" when it proceeds from one end of its range to the other with no reversals of direction. For example, in a descending monotonic scan, the atomic mass at which a measurement is taken can not be greater than the atomic mass at which previous measurements were taken during that scan. Since there is still some stabilization overhead associated with increasing and decreasing scanning speed, the survey mode is not used for very short blank regions. This dual-mode strategy can be applied to successive scans which are descending, ascending, or alternately ascending and descending.

In addition, if the map indicates a switch to the survey mode but the signal is rising, indicating a possible peak, the switch to the survey mode is delayed until the peak has passed or been found to be too small. Due to the presence of carbon and other isotopes, peaks tend to occur in clusters. The preferred strategy takes advantage of this by carefully measuring the range just above and below one or more peaks of interest.

The present invention provides several advantages. Because of its faster cycling time, the monotonic survey/measurement scan provides greater temporal peak-shape resolution than single measurement mode scanning. Generally, the monotonic survey/measurement scan approach can detect every peak that lasts long enough for characterization using a simple measurement mode. The survey mode is very fast when there are no peaks, which means when a peak elutes from a gas chromatograph, a survey scan will generally begin just as the peak begins. This renders unlikely the phenomenon occurring in simple measurement mode scanning where a mass spectrum is only half there because the peak began arriving half way through the scan.

Since survey scanning takes very little time to measure empty areas, there is little reason to limit scan range. Full spectra can be acquired along with high chromatographic peak-shape resolution. Survey scanning speed is, to a first approximation, proportional to the number of peaks found, not to the mass range. One can increase the scan rate significantly by raising the threshold so that fewer peaks are found. This allows a new tradeoff, i.e., scan rate versus peak threshold, that is not available using the measurement mode alone. Since much of a spectrum is scanned fast in the survey mode, there is flexibility to use higher resolution measurement scans in the areas of interest and still maintain high peak shape resolution.

The implemented strategy permits scan optimization without requiring separate survey scans, although a series of scans can advantageously begin with a survey scan. The mass filter is never abruptly changed, in either mode or in switching between modes. Thus, some of the limitations of strategies which introduce scan jumps and reversals are overcome. Other features and advantages of the present invention are apparent in the context of the description below with reference to the following figures.

DESCRIPTION OF THE PREFERRED EMBODIMENTS

Figure 1:
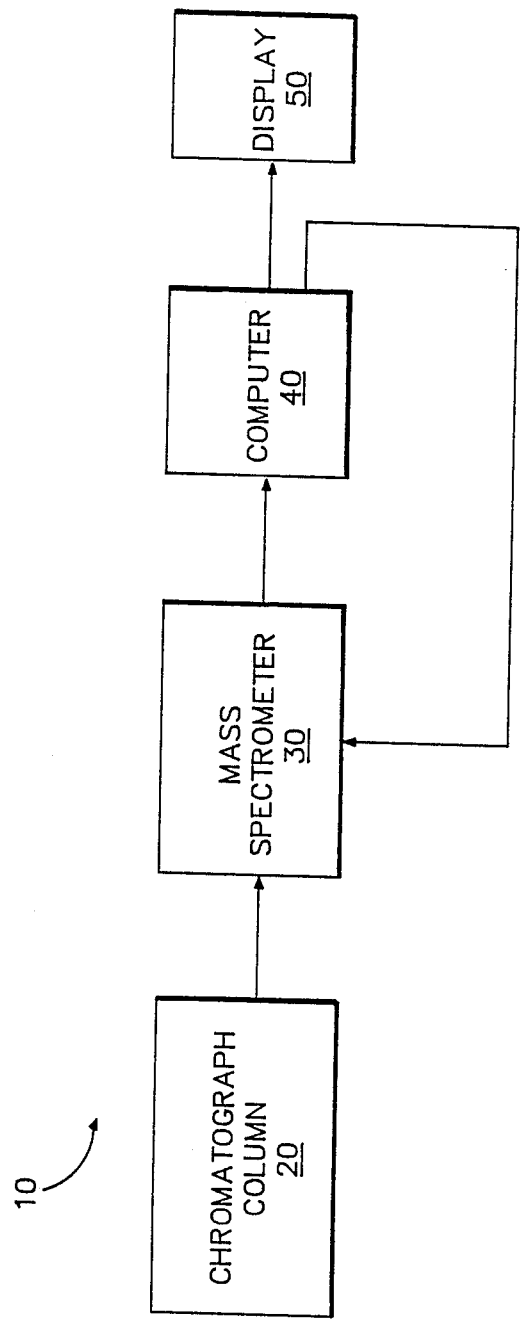
FIG. 1 is a block diagram of a gas chromatography and mass spectrometry system in accordance with the present invention.

A chromatography system 10 comprises a chromatograph column 20, a mass spectrometer 30, a computer 40 and a display 50. The output of the chromatograph column 20 is an evolving sample of gaseous mixture components. The mass spectrometer 30 provides a series of mass spectra of the eluting components to the computer 40. The computer 40 stores the spectra resulting from each scan, and generates a signal/blank scan map for the succeeding scan. The results of each scan, and of various statistical analyses performed upon the series of scans, can be provided at display 50. The map is used to control the mass spectrometer 30 to determine the switching between survey and measurement modes.

In an illustrative application of the present invention, the eluents from a gas chromatography system are analyzed with a mass spectrometer with a scan range, for example, of 800 to 50 daltons. The measurement mode can proceed anywhere from a very slow rate to about 1500 daltons per second, with 800 daltons per second being a typical rate. The survey mode can proceed at about 10 times this rate, e.g., 8000 daltons per second. The survey mode can use 1 dalton steps and a 2 dalton full width at half maximum (FWHM) peak width, while the measurement mode can use 0.1 dalton steps and 0.6 dalton FWHM peak width. The peak detection threshold criterion for the measurement mode is highly application dependent and can be varied as a function of mass. A threshold criterion for the survey mode can be set to about one half the measurement mode threshold criterion selected. For some mass filters, the peak detection threshold inherently lowers when the peak width is increased, so no special adjustment need be made for peak threshold.

Since there is overhead associated with switching modes, the measurement mode is used unless there is a gap of at least 4 daltons. To give the mass filter plenty of time to stabilize, the switch to the measurement mode takes place 2 daltons above the place where a peak is expected. The measurement mode continues until at least 1 dalton below where the last peak of a group is expected. Preferably, the switch to the survey mode can be delayed up to one additional dalton if the signal is rising, indicating a possible peak; once the peak is passed or has been found to be too low, the survey mode is entered. These rules ensure that the measurement mode is used whenever there is any chance of finding a peak; the survey mode is used when there really is nothing.

There is an additional reason for switching to the measurement mode 2 daltons above a suspected peak. Many peaks have carbon isotopes 1 dalton above them. If the survey mode detects a peak which is just eluting, it is possible that a carbon-13 isotope is present, but is too small for the survey mode to detect. By switching to the measurement mode 2 daltons above the peak found, there is time for the mass filter to stabilize and to measure precisely any isotopes that might be present.

Figure 2:
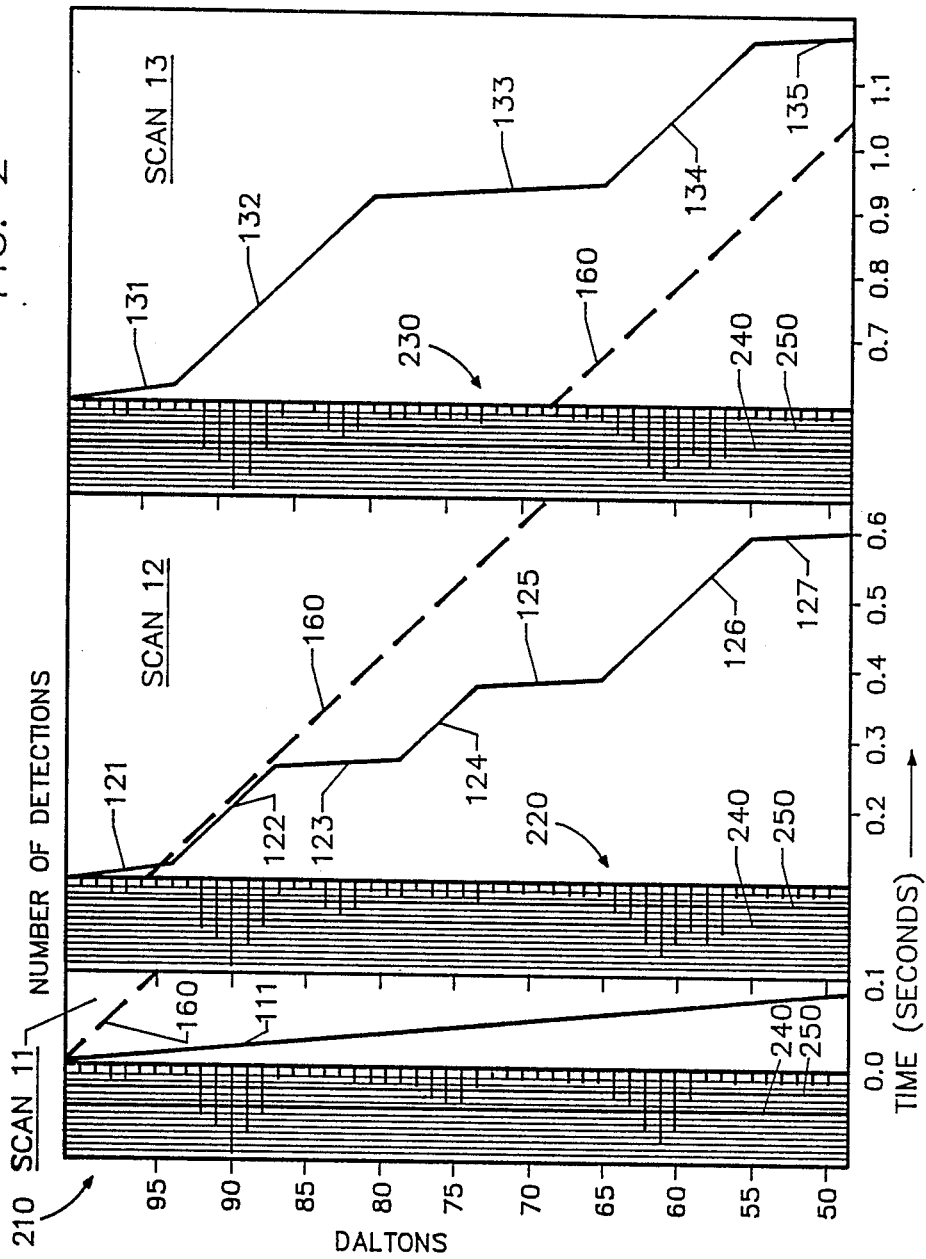
FIG. 2 is a graph depicting three scan cycles of a mass spectrometer along with the spectra of the components being scanned in accordance with the present invention.

Illustrating the scan strategy used in the present invention, an initial survey scan 11, a preceding scan 12 of two mixed survey/measure scans, and a succeeding scan 13 of the two mixed survey/measure scans are shown in FIG. 2. For expository purposes, hypothetical data is presented in the form of mass measurements taken at one dalton intervals over a mass range of 50 to 99 daltons.

FIG. 2 interleaves time lines and spectra. The two graphic forms share a vertical coordinate representing mass in daltons. The horizontal axis for the spectra represents the number of detections per unit time for a given mass. The horizontal axis for the time lines represents seconds of time.

The single steeply descending solid line 111 of scan 11 represents a survey mode scan of the entire mass range from 99 daltons to 50 daltons. Scan 11 is the initial scan of a series of scans, so no prior data is available to indicate where peaks of interest might be found. Scans 12 and 13 consist of alternating steep and gradual scan segments, e.g., 121-127 and 131-135; the steep (odd numbered) segments correspond to scan segments with the survey mode active, while gradual (even numbered) segments correspond to an active measurement mode. A broken line 160 descending gradually across the graph represents a single measurement mode scan over the full range for comparison purposes.

Spectra 210, 220 and 230 represent the readings that would be obtained during a scan, provided the measurement mode is active. Preferably, data below a measurement threshold 240 is discarded as noise in the measurement mode. In the survey mode, a binary determination is made as to whether a signal is above or below a survey threshold 250, and this determination is used to construct the map used in the next scan. Preferably, the survey threshold 250 is below the measurement threshold 240 to take into account the lower accuracy and the evolution of the sample between scans. In FIG. 2, the survey threshold 250 is one half the measurement threshold. Since the map for the next scan must rely on measurement mode data as well as survey mode data, the survey threshold 250 is used also in the measurement mode for purposes of defining the signal and blank regions.

During the initial survey scan 11, it is determined that range segments 99-92, 86-77, 73-65, and 58-50 represent blank regions of the 99-50 range. Not all of the remaining measurements would be above the measurement threshold 240; see, for example, the data at masses 76-74, 67, 66 and 59. However, these values are above the survey threshold 250, and have a greater likelihood than the masses in the blank segments of increasing to the measurement threshold 240 in one scan cycle.

Scan 12 consists of alternating survey and measurement scan segments. The first survey scan segment 121 corresponds to the first blank region at masses 99-92 detected during initial survey scan 11. However, the switch to the first measurement mode segment 122 occurs at about mass 94. In the present implementation of the invention, switching to the measurement mode takes place about two daltons before a blank region is exited. This guarantees stabilization before reaching the signal region for which measurement is indicated. Actually, stabilization can occur within half the two dalton reserve, so the last dalton, at mass 92, of a blank region can be measured along with the subsequent masses.

The first measurement mode scan segment 122 extends from mass 93 to mass 86. Stabilization occurs in time for a measurement at mass 92. However, the signal at this mass 94 is below measurement threshold 240, and so this data is not treated as positive spectral data. Measurement at masses 91 through 87 yields data above measurement threshold. Measurement mode is extended to mass 86, one dalton below the signal region.

The spectrometer returns to the survey mode at scan segment 123 between masses 86 and 78 within the second blank region determined during the initial survey scan 111. A change in the data at masses 83-81 causes a signal region to be indicated. This information is used with the effect that scan 13 is different from scan 12 in this region.

The next measurement scan segment 124 encompasses positively indicated masses 76-74, along with masses two daltons above and one dalton below, for reasons set forth above. Between scans of the 76-74 region, the mass indications dropped from between measurement threshold and survey threshold to below survey threshold. With or without this decrease, the data in this range is below measurement threshold and is not positively recorded in the mass spectrum provided by scan 12. However, since the data is now below survey threshold, the region including masses 76-74 is treated as a blank region during the next scan 13.

The survey mode returns for scan segment 125 to correspond to the third blank region detected in the initial survey scan 11. There is no change in the data between masses 73-65. However, due to the decreases in the masses immediately above, the original blank region including these masses is merged with the new region defined above for the next scan 13.

The next measurement scan segment 126 begins two daltons above the next mass 64 which was above survey threshold during the initial scan. The data taken at masses 66, 65, 64 and 63 is rejected as below measurement threshold 240. Positive measurements are made at masses 62-60 which have remained unchanged and above measurement threshold 240. Mass 59 is measured since it was above survey threshold during scan 11; the corresponding number of detections has increased to above measurement threshold for scan 12, so a positive measurement is recorded.

Measurement is taken of mass 58 since it is only one dalton below the adjacent non-blank region as determined during scan 11. The reading at this mass 58 has increased to above measurement threshold so a positive reading is made. This positive reading is exceptional and triggers a continuation of the measurement mode for one more dalton. This continuation results in a positive reading in newly evolved data at mass 57. In the present implementation, the exception allows a maximum of one extra dalton of the measurement mode, so the next scan segment 127 begins at mass 56 and extends to mass 50 at the bottom of the range.

Reviewing scan 12, positive measurements are made for all possible readings above measurement threshold 240. In addition, scan 12 has provided a map for determining the arrangement of survey and measurement segments during the next scan 13. As determined during scan 12, scan 13 consists of alternating survey and measurement scan segments 131, 132, 133, 134 and 135. Again, the slope of the segments corresponds to the mode. No changes in the spectrum are shown between scan 12 and scan 13 so no exceptions are triggered to extend either of the measurement mode segments 132 or 134.

Note that scan 13, which represents the second completed scan in which measurements were taken terminates only slightly beyond the time a first solely measurement mode scan would have ended, as indicated by the straight broken line 160. This indicates a factor of almost two improvement in peak shape resolution.

From the comparison provided, it can be seen that with respect to the hypothetical data, the survey/scan strategy provides a nearly 100% increase in scan frequency. This must be qualified since the intermediate backscans for the survey/measurement mode are not represented on the graph. On the other hand, succeeding cycles do not require an initial survey scan, such as scan 11. FIG. 2 may be conservative in its comparison, since most data is more sparse than that shown, a condition strongly favoring an optimization strategy over a measurement mode only approach.

A comparison using more realistic data provides even better results. For example, consider a compound which contains 100 peaks over a range of 800-50 daltons, using 2 A/D samples at 50 microseconds at each mass. In the areas above survey threshold, measurement mode scanning proceeds at 800 daltons per second. Assuming, for simplicity, the peaks are arranged in pairs, there are 50 areas each 2 daltons wide to scan, plus two daltons above and 1 dalton below for a total of 250 daltons. This consumes 250/800 or 0.313 seconds. The survey mode applies to the remaining 500 daltons and use about 0.063 seconds. The total is about 0.355 seconds, versus almost 1 second for simple measurement mode, yielding an almost 3 to 1 improvement in scan rate. The comparison would be less dramatic for denser spectra and more dramatic in the case of more sparsely populated spectra.

Many variations and modifications of the above embodiments are provided for by the present invention. The invention is not limited to gas chromatography plus mass spectrometry systems. It applies generally where mixed measurement and survey modes can be used to improve temporal resolution, especially in systems where monotonic scanning is preferred. Different spectrometers, mass filters, chromatographic systems, computational systems and output devices are provided for. Different ranges, scan rates, peak widths and thresholds can be used. Pulse width detection and peak detection thresholds can be varied over a scan. While, in general, "blank" refers to regions in which the signal remains below a predetermined threshold, "blank" can also be applied to regions which are not of interest for some other reason. While the illustrated embodiment employs descending scans, ascending scans and alternately ascending and descending scans can be used. These and other variations are provided for by the present invention, the scope of which is limited only by the following claims.

What is claimed is:

1. A system comprising:
   means for receiving a sample;
   scanning means for repeatedly monotonically scanning said sample over a predetermined scanning range so as to obtain a series of spectra, said scanning means having alternate survey and measurement modes, said survey mode being characterized by a faster scanning rate than said measurement mode;
   output means for indicating spectral data gathered during the measurement mode for each scan taken by said scanning means;
   map means for generating a map during a scan by said scanning means so that said predetermined scanning range is divided into signal and blank regions according to a predetermined threshold criterion; and
   mode means for switching between said survey mode and said measurement mode during a monotonic scan over said predetermined scanning range by said scanning means at least in part as a function of the map generated by said map means during a preceding scan over said predetermined scanning range;
   wherein a spectral chromatogram can be obtained using a series of monotonic scans, said series including at least some scans serving the dual functions of measuring in accordance with a map generated by a preceding scan and of surveying to generate a map to be used by a succeeding scan.

2. The system of claim 1 wherein said mode means further comprises means for switching modes only within blank regions of a map.

3. The system of claim 1 further comprising override means for delaying a switch to survey mode as indicated by a map according to a predetermined exception criterion evaluated during a present measurement mode.

4. The system of claim 1 wherein said scanning means further includes resolution means so that the resolution of said scanning means during said measurement mode can be greater than the resolution during said survey mode.

5. A method comprising:
   introducing a sample into a spectrometer;
   scanning said sample repeatedly and monotonically over a predetermined spectral range;
   during each of several successive scans, generating a map indicating signal and blank regions according to a predetermined threshold criterion;
   during the succeeding scan, switching between survey and measurement mode as determined at least in part by the map generated during the preceding scan; and
   outputting as data measurements taken during measurement mode operation within each scan.

6. The method of claim 5 wherein, for each of several successive scans, mode switching occurs only in blank regions as indicated by the map generated during the preceding scan, said survey mode being used only within blank regions as indicated by the map generated during the preceding scan.

7. The method of claim 5 wherein, for a given scan while in measurement mode, a switch to survey mode is delayed according to a predetermined exception criterion based on data collected in the present measurement mode.

8. The method of claim 5 wherein the resolution during measurement mode is greater than the resolution during survey mode.

* * * * *